(12) United States Patent
Zerhusen et al.

(10) Patent No.: US 11,723,822 B2
(45) Date of Patent: Aug. 15, 2023

(54) SECURITY LATCH FOR USER INTERFACE HOUSING

(71) Applicant: Hill-Rom Services, Inc., Batesville, IN (US)

(72) Inventors: Robert Mark Zerhusen, Cincinnati, OH (US); Jonathan Keith Moenter, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 393 days.

(21) Appl. No.: 16/923,341

(22) Filed: Jul. 8, 2020

(65) Prior Publication Data

US 2021/0007920 A1 Jan. 14, 2021

Related U.S. Application Data

(60) Provisional application No. 62/872,297, filed on Jul. 10, 2019.

(51) Int. Cl.
*A61G 7/05* (2006.01)
*A61G 13/10* (2006.01)
(Continued)

(52) U.S. Cl.
CPC ......... *A61G 7/0503* (2013.01); *A61G 13/101* (2013.01); *B60R 11/0252* (2013.01);
(Continued)

(58) Field of Classification Search
CPC ......... B60R 11/0252; B60R 2011/0288; B60R 11/00; G06F 1/1632; A61B 2560/0487;
(Continued)

(56) References Cited

U.S. PATENT DOCUMENTS

| 5,542,138 A | 8/1996 | Williams et al. |
| 10,028,875 B2 | 7/2018 | Hatch |
| (Continued) | | |

FOREIGN PATENT DOCUMENTS

WO 2010018011 A1 2/2010

OTHER PUBLICATIONS

"Tool." Vocabulary.com, www.dictionary.cambridge.org/us/dictionary/english/tool.*

*Primary Examiner* — David R Hare
*Assistant Examiner* — Madison Emanski
(74) *Attorney, Agent, or Firm* — Price Heneveld LLP

(57) ABSTRACT

A patient support apparatus includes a frame having a head end and a foot end. A support arm is operably coupled to the head end of the frame. A cord is coupled to the support arm. A user interface housing is operably coupled to the cord and configured to retain a user interface. The user interface housing includes a locking body coupled to a body of the user interface housing and has a flange configured to engage an edge of the user interface. A latch mechanism includes a flexible body coupled to a rear side of the locking body. The latch mechanism is configured to selectively secure the locking body in a position. A shelf is coupled to a lower portion of the body of the user interface housing. The shelf has stoppers operably coupled to the shelf. The stoppers are adjustable along a horizontal plane to define different widths.

15 Claims, 6 Drawing Sheets

(51) Int. Cl.
B60R 11/02 (2006.01)
F16M 13/02 (2006.01)

(52) U.S. Cl.
CPC ....... *F16M 13/022* (2013.01); *A61G 2203/20* (2013.01); *A61G 2203/70* (2013.01)

(58) Field of Classification Search
CPC .............. A61G 7/0503; A61G 2203/20; A61G 7/0524; A61G 13/101; F16M 13/022; F16M 2200/028; F16M 11/041; F16M 11/28; F16M 2200/024; F16M 13/00
See application file for complete search history.

(56) References Cited

U.S. PATENT DOCUMENTS

| | | | |
|---|---|---|---|
| 2010/0264182 A1* | 10/2010 | Perlman | H04M 1/04 224/409 |
| 2012/0312847 A1 | 12/2012 | LaColla et al. | |
| 2016/0008197 A1 | 1/2016 | Zerhusen et al. | |
| 2016/0324701 A1 | 11/2016 | Cambridge et al. | |
| 2017/0032650 A1 | 2/2017 | Wiggermann et al. | |
| 2018/0161225 A1 | 6/2018 | Zerhusen et al. | |
| 2018/0333317 A1 | 11/2018 | Zerhusen et al. | |

\* cited by examiner

SECURITY LATCH FOR USER INTERFACE HOUSING

CROSS-REFERENCE TO RELATED APPLICATION

This application claims priority to and the benefit under 35 U.S.C. § 119(e) of U.S. Provisional Application No. 62/872,297, filed on Jul. 10, 2019, entitled "SECURITY LATCH FOR USER INTERFACE HOUSING," the disclosure of which is hereby incorporated herein by reference in its entirety.

FIELD OF THE DISCLOSURE

The present disclosure generally relates to a user interface housing for a patient support apparatus, and more specifically to a security latch for a user interface housing.

SUMMARY OF THE DISCLOSURE

According to one aspect of the present disclosure, a patient support apparatus includes a frame that has a head end and a foot end. A support arm is operably coupled to the head end of the frame. A cord is coupled to the support arm. A user interface housing is operably coupled to the cord and configured to retain a user interface. The user interface housing includes a locking body coupled to a body of the user interface housing and has a flange configured to engage an edge of the user interface. A latch mechanism includes a flexible body coupled to a rear side of the locking body. The latch mechanism is configured to selectively secure the locking body in a position. A shelf is coupled to a lower portion of the body of the user interface housing. The shelf has stoppers operably coupled to the shelf. The stoppers are adjustable along a horizontal plane to define different widths.

According to another aspect of the present disclosure, a user interface housing for a patient support apparatus includes a body that has an upper portion and a lower portion. First and second ribs extend between the upper portion and the lower portion. The first and second ribs define first and second channels, respectively. A locking body is slidably disposed between the first and second ribs. The locking body includes a latch mechanism configured to secure the locking body in position. The locking body defines an access notch configured to receive a tool for selectively releasing the latch mechanism.

According to another aspect of the present disclosure, a user interface housing for a patient support apparatus includes a body that has an upper portion and a lower portion. First and second ribs extend between the upper portion and the lower portion. The first and second ribs define first and second channels, respectively. A locking body is slidably engaged with the first and second ribs and is adjustable between the upper and lower portions. The locking body defines an aperture. A button is operably coupled with the locking body. The button includes at least one rib configured to extend through the aperture on the locking body to selectively limit movement of the locking body.

These and other features, advantages, and objects of the present invention will be further understood and appreciated by those skilled in the art by reference to the following specification, claims, and appended drawings.

DETAILED DESCRIPTION

Figure 1:
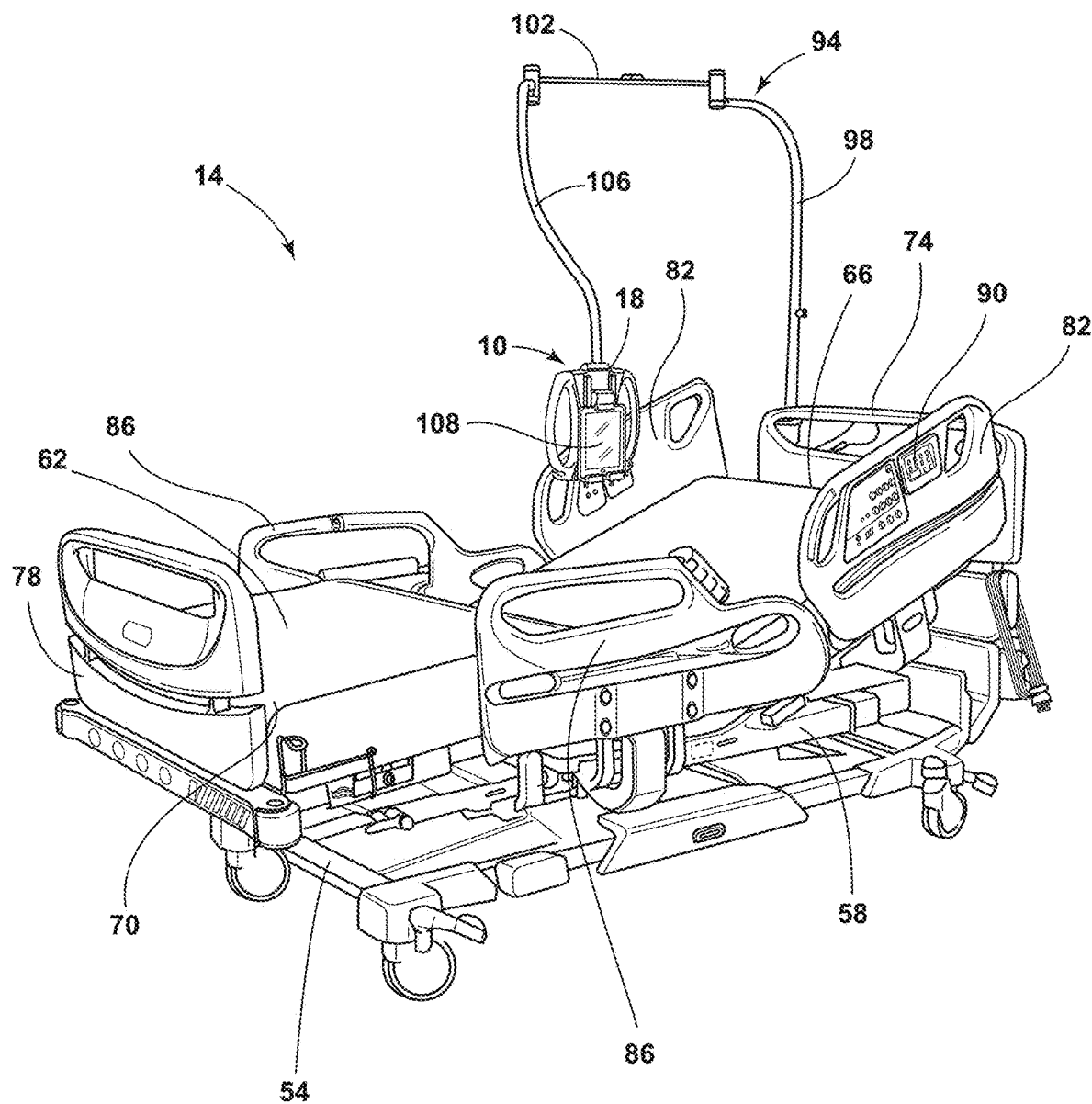
FIG. 1 is a top perspective view of a patient support apparatus, according to various aspects described herein.

The present illustrated embodiments reside primarily in combinations of method steps and apparatus components related to a user interface housing for a patient support apparatus. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-6, reference numeral 10 generally designates a user interface housing for a patient support apparatus 14. The user interface housing 10 includes a body 18 having an upper portion 22 and a lower portion 26. First and second ribs 30, 34 extend from the upper portion 22 towards the lower portion 26 and the first and second ribs 30, 34 define first and second channels 38, 42, respectively. A locking body 46 is slidably disposed between the first and second ribs 30, 34. The locking body 46 includes a latch mechanism 50 configured to secure the locking body 46 in position.

Referring now to FIG. 1, the patient support apparatus 14 may include a hospital bed. While described as the patient support apparatus 14, it is within the scope of the disclosure that the patient support apparatus 14 may include a bed frame, a mattress, or any suitable structure for supporting a patient, including, but not limited to: other types of beds, surgical tables, examination tables, stretchers, recliners, and the like.

The patient support apparatus 14 may include a frame, which may be in the form of a base frame 54. An upper frame 58 may be coupled with the base frame 54. The upper frame 58 may be operable between raised, lowered, and tilted positions relative to the base frame 54. The patient support apparatus 14 may include a surface, such as a mattress 62 supported by one of the base frame 54 and the upper frame 58. The mattress 62 may be in the form of a cushion including a foam base and multiple layers.

The patient support apparatus 14 includes a head end 66 and a foot end 70. A headboard 74 is provided at the head end 66 and a footboard 78 is provided at the foot end 70. The patient support apparatus 14 may include a pair of head siderail assemblies 82 and a pair of foot siderail assemblies 86. In some examples, an interface 90, which may be a graphical user interface, may be coupled to an external side of at least one siderail of the head and foot siderail assemblies 82, 86.

As illustrated in FIG. 1, a support arm 94 is coupled with the head end 66 of the patient support apparatus 14. Alternatively, the support arm 94 may be coupled with of at least one siderail of the head and foot siderail assemblies 82, 86, or with one of the base frame 54 and the upper frame 58, but is not limited to such examples. The support arm 94 generally includes a fixed portion 98 and a pivotable portion 102. The pivotable portion 102 extends laterally from the fixed portion 98 and is configured to rotate relative to the fixed portion 98.

A strand, or cord 106, may depend from the pivotable portion 102 and may be repositioned to a variety of locations about the patient support apparatus 14. The user interface housing 10 may be coupled with the cord 106. The pivotable portion 102 and/or the cord 106 generally has exceptional flexibility to provide support for accessing the user interface housing 10 at different angles and positions relative to the patient support apparatus 14. However, the user interface housing 10 may be integrated with any suitable component of the patient support apparatus 14.

A user interface 108 is secured to the user interface housing 10, which may be used by a caregiver or a patient. The user interface 108 may be in the form of a touch screen tablet computer, a smartphone, and the like, which may be generally rectangular in shape. However, it is also contemplated that the user interface 108 may be of various shapes, which can be secured to the user interface housing 10.

Figure 2:
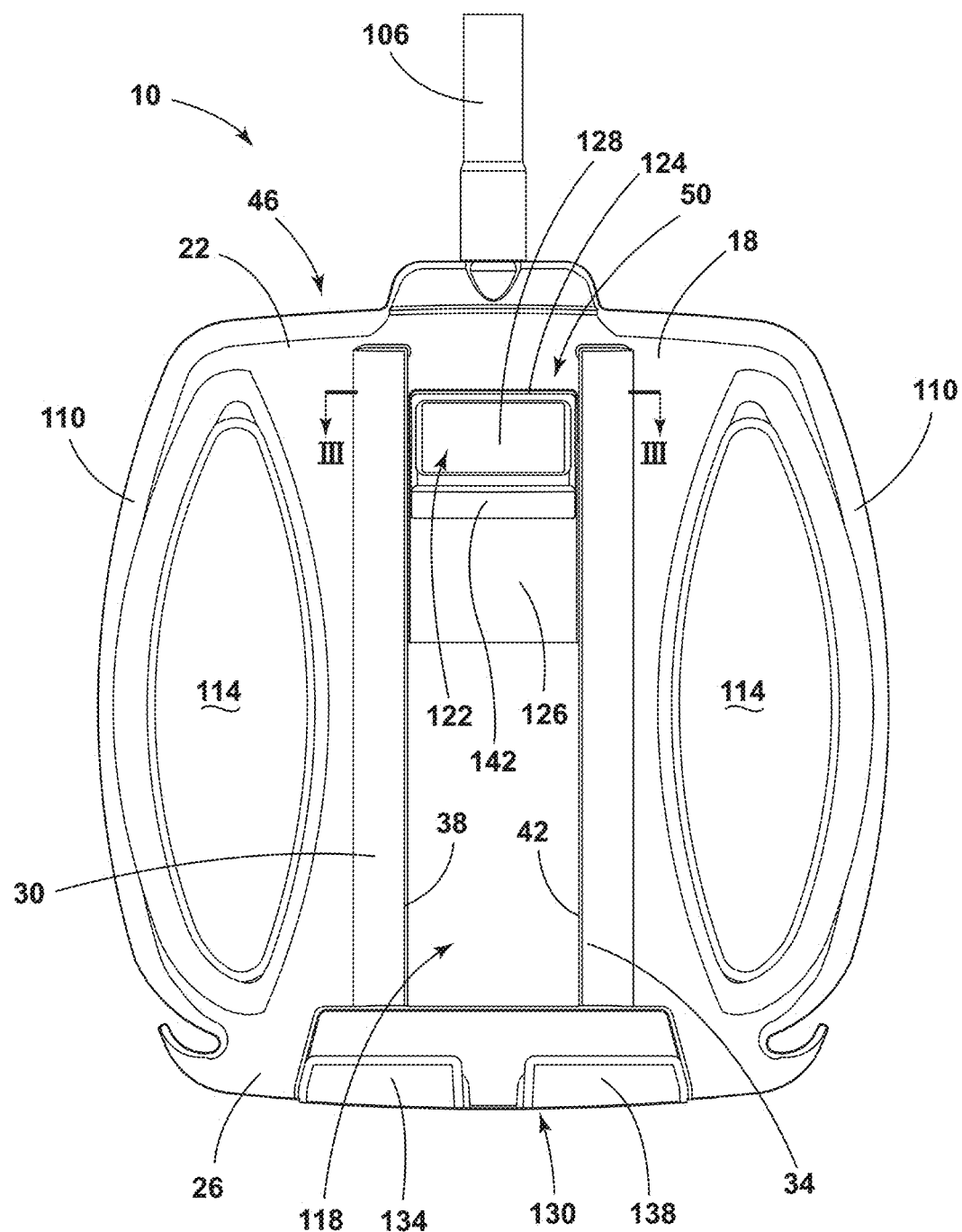
FIG. 2 is a front elevational view of a user interface housing, according to various aspects described herein.

Referring now to FIG. 2, the user interface housing 10 is illustrated without the user interface 108. The body 18 of the illustrated user interface housing 10 includes at least one gripping surface 110, which may include one or more handles 110. As illustrated, the user interface housing 10 includes two handles 110 that each extend from the upper portion 22 to the lower portion 26 of the body 18. The handles 110 may be covered in a material, such as a soft, silicone to provide an enhanced gripping surface and which is easily cleanable.

In some examples, as illustrated in FIG. 2, the handles 110 extend outwardly from the body 18 to define apertures 114. The apertures 114 are generally oval, elliptical, or lanceolate shaped and may be dimensioned such that a hand of a user can reach at least partially through one of the apertures 114, which may be beneficial for grasping the body 18 or one of the handles 110. The first and second ribs 30, 34 defining the first and second channels 38, 42 are disposed on a middle portion 118 of the body 18, which may be located between the apertures 114. However, it is within the scope of this disclosure for the user interface housing 10 to include alternative gripping arrangements, which may or may not include the apertures 114. For example, one or more handlebars, cup handles, pull handles, or knobs, etc. may extend from the body 18 to facilitate moving and gripping of the user interface housing 10.

Still referring to FIG. 2, a latch actuator 122 is operably coupled with the latch mechanism 50 for selectively releasing the locking body 46, which enables the locking body 46 to be slidable within the first and second channels 38, 42. At least a portion of the latch mechanism 50 may be disposed within an interior of an upper end 124 of the locking body 46. The upper end 124 may be in the form of a curved body that extends outwardly from a planar portion 126 of the locking body 46. Alternatively, the upper end 124 may be any suitable shape, which may be rectangular or flat and may include a non-slip cleanable surface.

In various examples, the latch actuator 122 includes a button 128, which may be generally flush with the upper end 124. Thus, the button 128 generally includes a shape complementary to the shape of the upper end 124. In addition to the button 128 being flush with the upper end 124, molding the button 128 in the same color as the locking body 46 may provide the aesthetically pleasing appearance of a seamless interface between the button 128 and the locking body 46. Moreover, the button 128 generally has a continuously arcuate outer surface, which contributes to the seamless interface between the button 128 and the locking body 46. While illustrated as the button 128, the latch actuator 122 may include any suitable component for actuating the latch mechanism 50, which may include, but not limited to: a tab, a handle, a push-button, a toggle, etc.

As shown in FIG. 2, a shelf 130 is coupled with the lower portion 26 of the body 18, which is dimensioned to receive an edge, which may be a lower edge, of the user interface 108 (FIG. 1). The shelf 130 includes a first shelf portion 134 and a second shelf portion 138, which extend upwards to retain the edge of the user interface 108. However, the shelf 130 may be in any suitable configuration that provides a surface for the user interface 108, which may include a single, continuous portion and may or may not extend upwardly.

Figure 4:
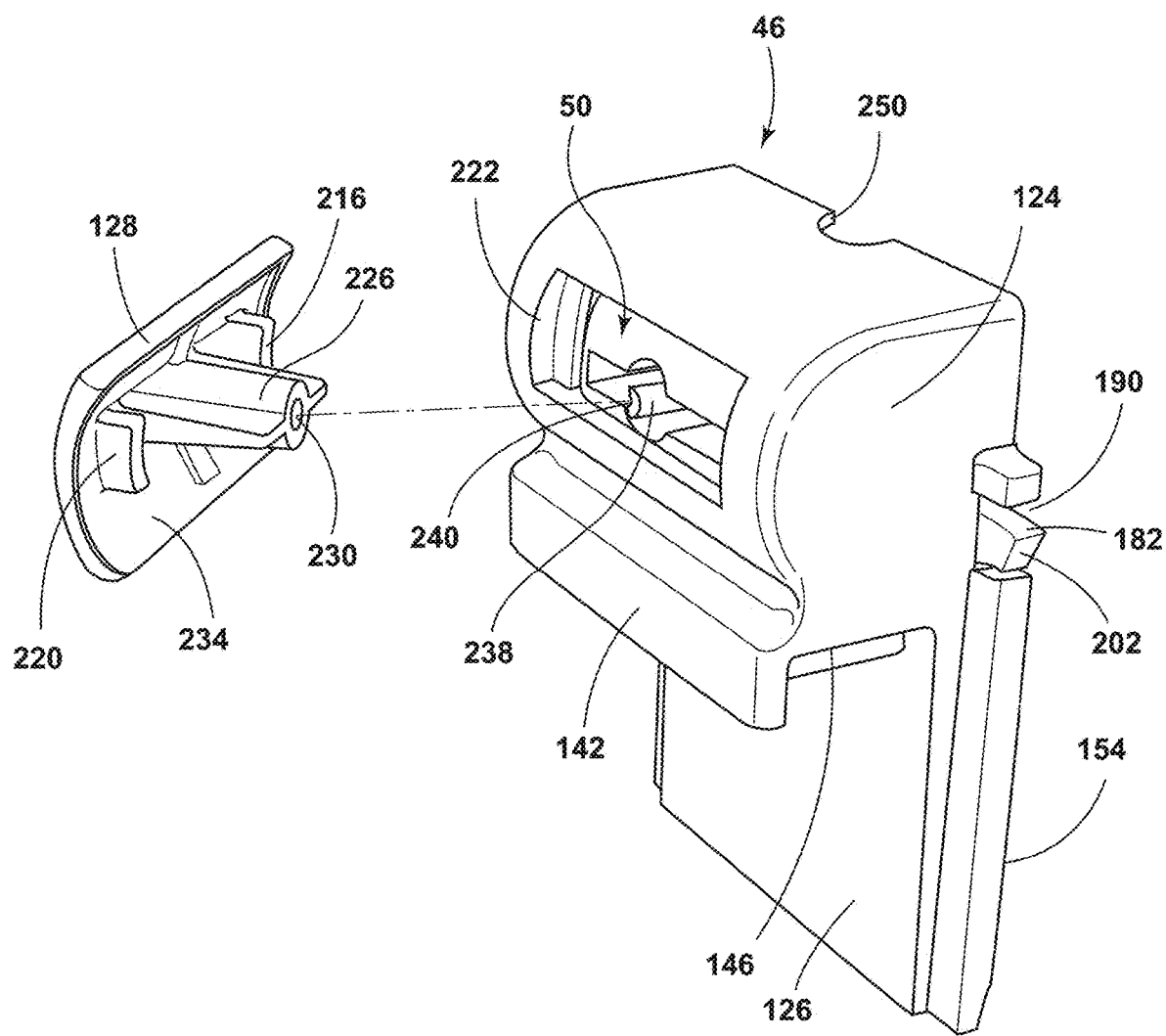
FIG. 4 is a top perspective view of a button separated from a locking body, according to various aspects described herein.

Additionally, the locking body 46 includes a flange 142, which extends downwardly from the latch actuator 122 thereby defining a recess 146 (FIG. 4). The recess 146 is dimensioned to receive another edge of the user interface 108, which may be an upper edge. The height, or position, of the flange 142 and the recess 146 is adjusted by repositioning the locking body 46. Thus, the user interface 108 may be secured to the user interface housing 10 in a clamping manner by way of the shelf 130 and the flange 142. In this way, the user interface housing 10 may accommodate a user interface 108 of a variety of sizes.

Figure 3:
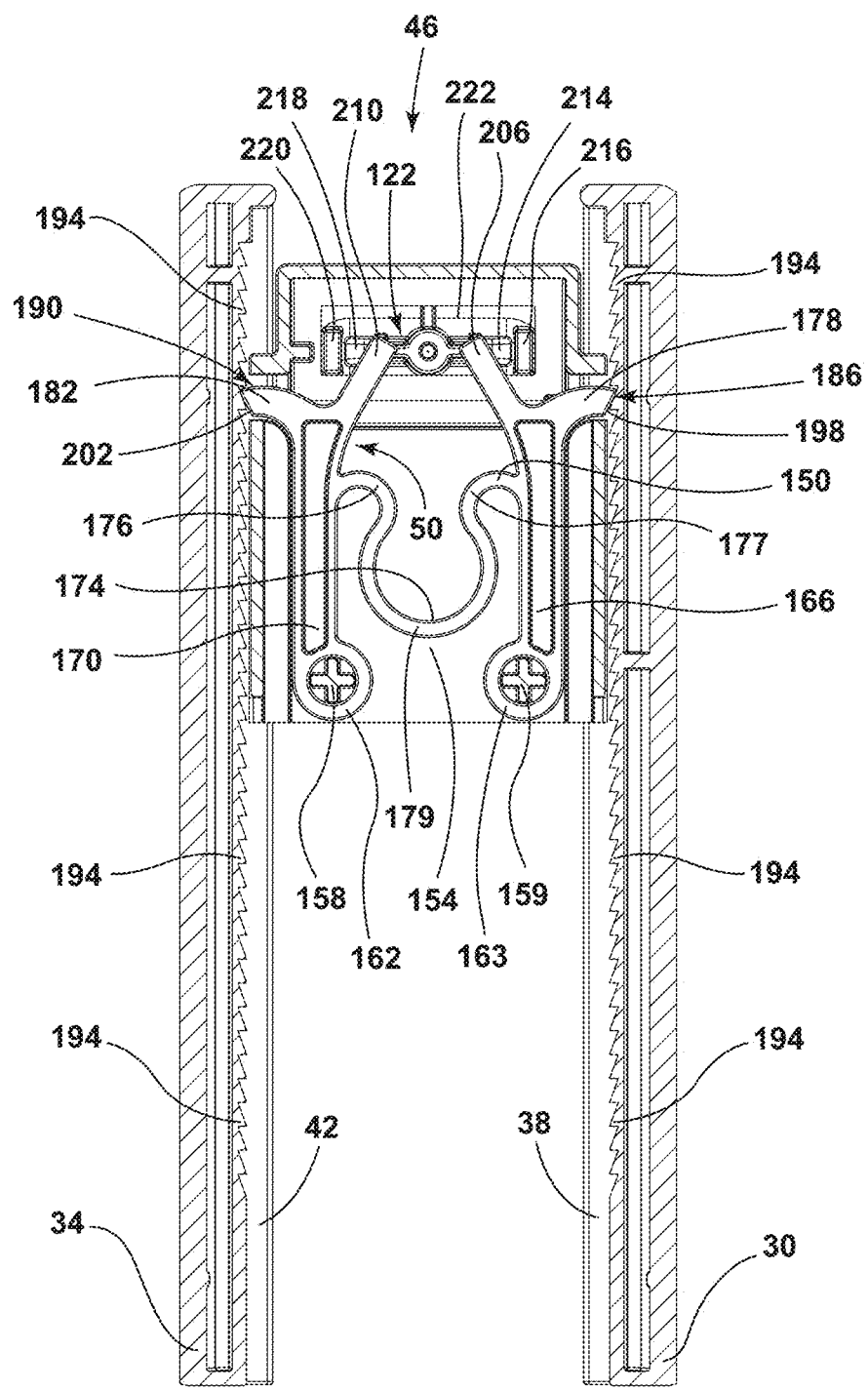
FIG. 3 is a front elevational cross-sectional view of a latch mechanism along line III-Ill of FIG. 2, according to various aspects described herein.

FIG. 3 is a cross-sectional view of the latch mechanism 50 along line III-Ill of FIG. 2, more clearly illustrating the first and second channels 38, 42. The latch mechanism 50 includes a flexible body 150 coupled to a rear side 154 of the locking body 46. The flexible body 150 may be made of any suitable material configured to be deformed elastically. The flexible body 150 may be fastened to the rear side 154 via first and second molded bosses 158, 159. In this example, the flexible body 150 includes first and second loops 162, 163 configured to stretch over the first and second bosses 158, 159, respectively, to form a taut connection. However, it is within the scope of this disclosure for the flexible body 150 to be coupled to the locking body 46 via any suitable fastening technique including adhesives, co-molding, fasteners, and the like.

The flexible body 150 generally includes a first body portion 166 laterally spaced from a second body portion 170, which is coupled to one another with a connecting portion 174. The connecting portion 174 includes first and second arcs 176, 177 coupled with the first and second body portions 166, 170. The first and second arcs 176, 177 may be coupled via a bight portion 179, which may be generally concave up while the first and second arcs 176, 177 may be generally concave down. Furthermore, the bight portion 179 may include a larger perimeter than each of the first and second arcs 176, 177. The arcuate construction of these features allows for increased flexibility resulting in a robust system that can be locked and unlocked over many cycles. In various examples, the connecting portion 174 may be generally U-shaped. However, the connecting portion 174 may be generally horizontal, V-shaped, etc.

Still referring to FIG. 3, the first and second body portions 166, 170 extend substantially along the height of the rear side 154 of the locking body 46. Furthermore, the first and second body portions 166, 170 include first and second projections 178, 182, respectively. The first and second projections 178, 182 extend from the first and second body portions 166, 170 towards first and second apertures 186, 190 on the locking body 46, respectively. Accordingly, the first and second projections are laterally spaced from one another on opposing sides of the locking body 46 and generally extend outward, away from one another. The first and second apertures 186, 190 may be positioned on the side of the locking body 46 adjacent the channels 38, 42, respectively. The first and second channels 38, 42 each include a ratcheting mechanism, which may include a plurality of vertically spaced teeth 194. Each tooth 194 defines a tooth surface, which may be in the form of a sloped surface. The first and second projections 178, 182 terminate in angled edges 198, 202, respectively, which are generally complementary to the surface of each tooth 194, thereby forming a pawl.

In a locked or extended position, as illustrated in FIG. 3, the first and second projections 178, 182 extend outwardly from the first and second apertures 186, 190, and engage at least one tooth surface. Thus, the first and second projections 178, 182 may catch against a steeply sloped edge of the engaged teeth 194 and prevent any further motion in an upward direction. However, the locking body 46 may be pushed downwardly in the locked position to secure the user interface 108 between the shelf 130 and the recess 146. In this way, the locking body 46 may be pushed downwards until the upper edge of the user interface 108 contacts the locking body 46 within the recess 146 and prevents further downward movement.

The flexible body 150 further includes a first flexible tab 206 and a second flexible tab 210 coupled with the first and second projections 178, 182, respectively. The first and second flexible tabs 206, 210 are angled inwardly such that first and second flexible tabs 206, 210 extend towards each other. Furthermore, the latch actuator 122 may be operably coupled with a first shaft 214 and a second shaft 218 disposed adjacent to the first and second flexible tabs 206, 210 respectively. The first and second shafts 214, 218 are generally disposed outward from the first and second flexible tabs 206, 210 with the first and second flexible tabs 206, 210 extending at least partially between the first and second shafts 214, 218. In the locked, or extended position, the first and second shafts 214, 218 may be adjacent, or in contact with, the first and second flexible tabs 206, 210.

The latch actuator 122 may include a first rib 216 and a second rib 220 disposed within an aperture 222 defined by the locking body 46. The ribs 216, 220 may be sized to extend substantially the height of the aperture 222 to limit or prevent up/down movement of the button 128. The first and second ribs 216, 220 are laterally spaced from one another and are generally positioned at opposing side edges of the aperture 222. Accordingly, the first and second shafts 214, 218 are each disposed between the first and second ribs 216, 220. The first and second ribs 216, 220 at least partially prevent movement of the first and second shafts 214, 218.

In examples where the ribs 216, 220 are not included on the latch actuator 122, to transition from the locked position to a released, or retracted position, the latch actuator 122 may be shifted upwardly, which may in turn shift the first and second shafts 214, 218 downward. Thus, the first and second shafts 214, 218 may contact and push down on the first and second flexible tabs 206, 210, such that the first and second flexible tabs 206, 210 are pressed more closely towards each other against a biasing force of the flexible body 150. In this way, a space between the first and second flexible tabs 206, 210 is decreased. Due to the elastic properties of the flexible body 150, the first and second projections 178, 182 can be pulled inwards upon movement of the first and second flexible tabs 206, 210 inwards. Thus, upon sufficient movement inwards, the first and second projections 178, 182 do not engage the tooth 194 and the locking body 46 may slide unrestricted between the upper portion 22 and the lower portion 26 of the body 18.

Referring now to FIG. 4, the locking body 46 and the stationary button 128 are more clearly illustrated. In some examples, the button 128 may include a column 226 defining a channel 230 positioned on a rear side 234 thereof. The channel 230 is sized to receive a shaft 238 coupled with the latch mechanism 50 in order to couple the button 128 to the latch mechanism 50. The shaft 238 includes a keyed portion 240 complementary to the shape of the channel 230 to facilitate proper insertion of the button 128. However, the button 128 may be coupled with the latch mechanism 50 in any suitable configuration, which may include fasteners, clasps, snaps, magnets, etc. in order to form a non-permanent or permanent joint.

At least a portion of the latch mechanism 50 may be pivotable within the aperture 222 on the locking body 46. A spring 244 (FIG. 5A) facilitates pivoting of at least a portion of the latch mechanism 50. The ribs 216, 220 provided on the rear side 234 of the button 128 generally prevent the button 128 from sliding movement, thereby preventing pivoting of at least a portion of the latch mechanism 50. For example, as the ribs 216, 220 extend through the aperture 222 on the locking body 46, the ribs 216, 220 may prevent up/down movement of the button 128. Therefore, the button 128 may restrict pivoting of the latch mechanism 50 and, consequently, restricting or limiting movement of the locking body 46. The use of the button 128 may be beneficial in applications where locking/releasing the user interface 108 requires additional safeguarding.

Figure 5A:
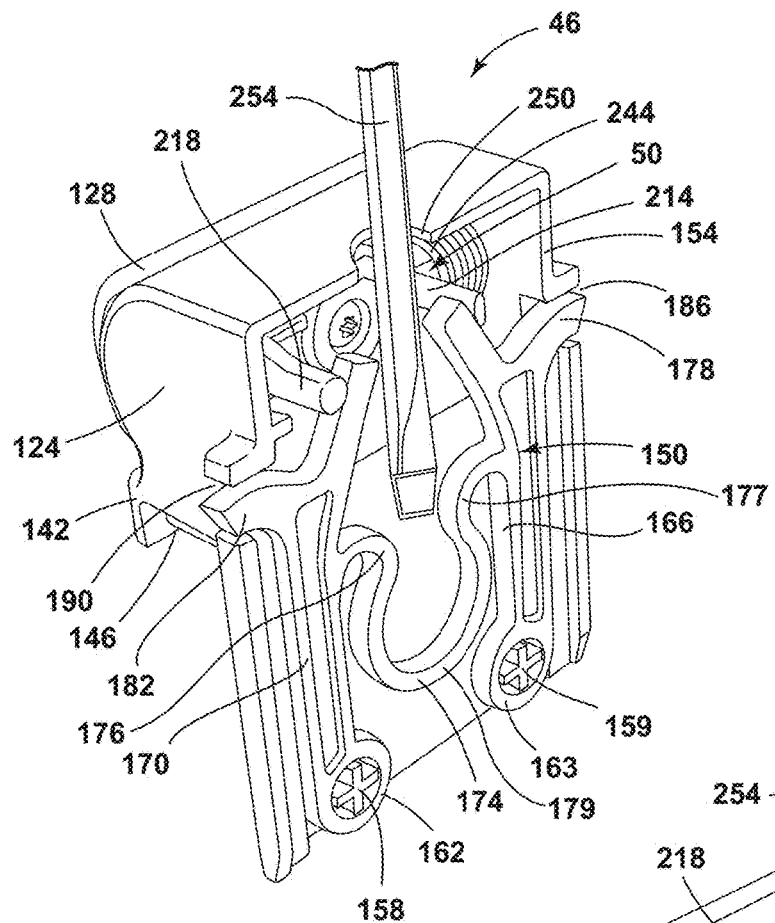
FIG. 5A is a rear perspective view of the locking body of FIG. 4, according to various aspects described herein.
Figure 5B:
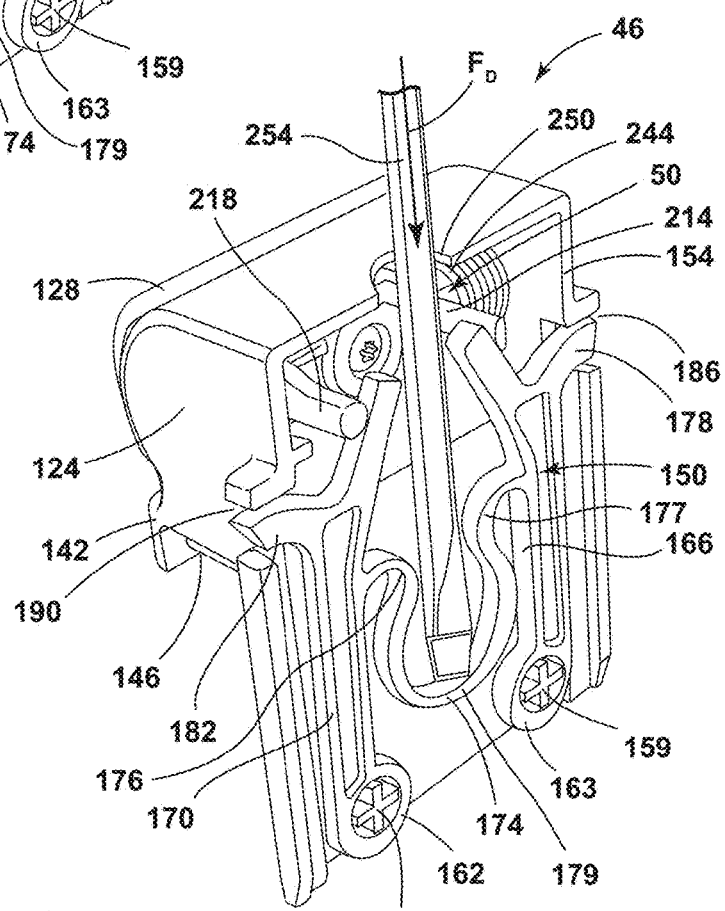
FIG. 5B is a rear perspective view of the locking body of FIG. 4, according to various aspects described herein.

FIGS. 5A and 5B illustrate an alternative technique for transitioning the locking body 46 from the locked position to the released position, which may be beneficial when the button 128 is coupled with the latch mechanism 50. The locking body 46 may define a recess, or an access notch 250 located on the rear side 154 at the upper end 124. The access notch 250 is configured to receive or allow a tool 254, such as a screwdriver, to access the rear side 154 of the locking body 46 when mounted to the user interface housing 10. The tool 254 may be any suitable tool configured to access the rear side 154, which may include a tool having a sufficient length and width to fit through the access notch 250 and reach the connecting portion 174. FIG. 5A illustrates the flexible body 150 in the extended position where the first and second projections 178, 182 extend outwardly from the first and second apertures 186, 190.

FIG. 5B illustrates the flexible body 150 in the retracted position. Application of a predetermined force, $F_D$, by the tool 254 adjusts the latch mechanism 50 from the extended position to the retracted position. Application of the predetermined force, $F_D$ on the connecting portion 174 forces the connecting portion 174 downward, away from the first and second apertures 186, 190. As a result, the first projection 178 is rotated inwardly about the first boss 158 towards the connecting portion 174 such that the first projection 178 is withdrawn and no longer disposed within the first aperture 186. Likewise, application of the predetermined force, $F_D$, by the tool 254 on the connecting portion 174 rotates the second projection 182 inwardly about the second boss 159 towards the connecting portion 174, such that the second projection 182 is withdrawn and no longer disposed within the second aperture 190. The force, $F_D$, may be applied to the bight portion 179 of the connecting portion 174, which causes deformation of the bight portion 179 and the first and second arcs 176, 177. In this way, the bight portion 179 and the first and second arcs 176, 177 flex in order to draw in the first and second projections 178, 182.

Figure 6:
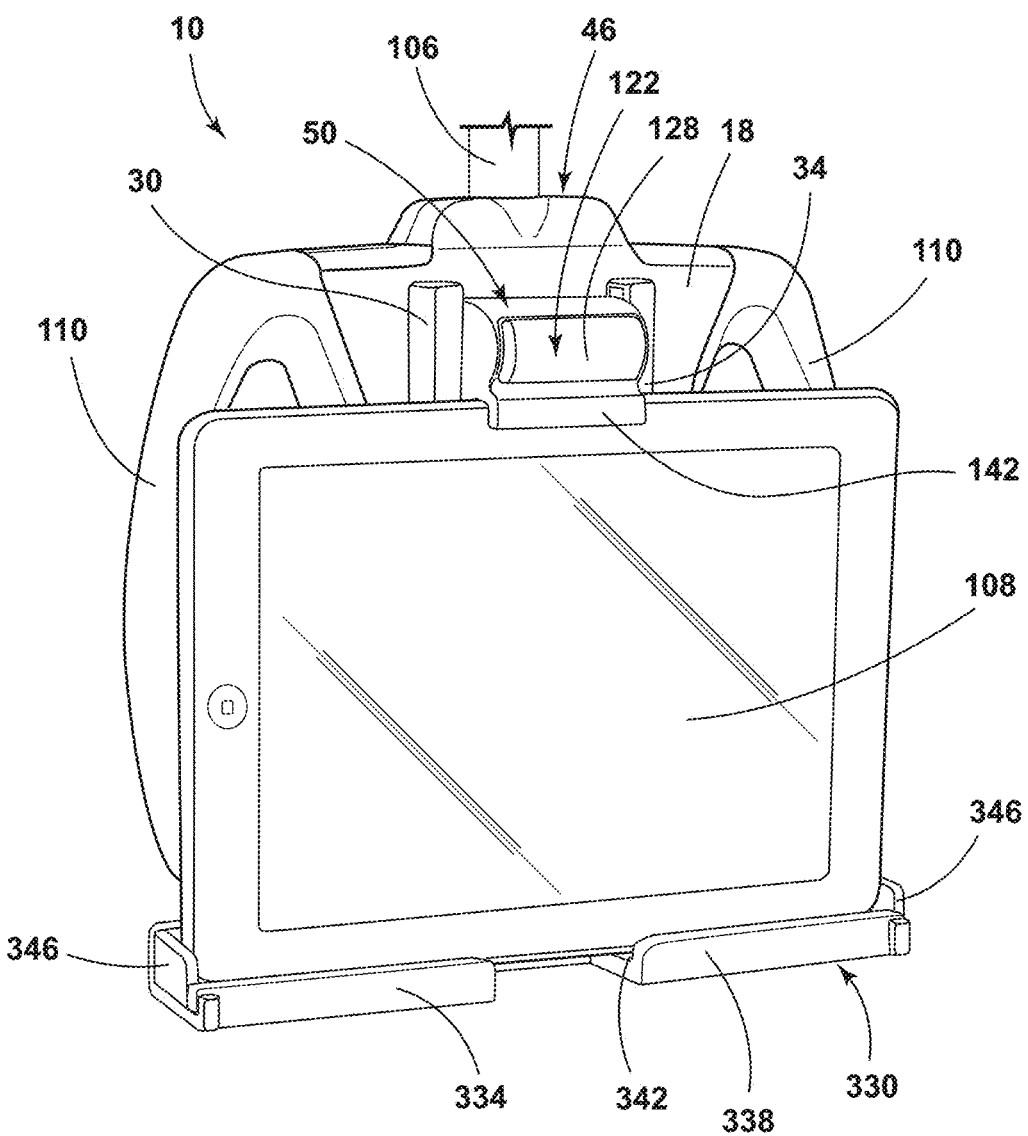
FIG. 6 is a front perspective view of a user interface housing, according to various aspects described herein.

Referring now to FIG. 6, the user interface housing 10 is illustrated with an additional or alternative configuration of a shelf 330. Similarly to the shelf 130, the shelf 330 includes a first shelf portion 334 and a second shelf portion 338, which extend upwards to retain the edge, which may be a lower portion, of the user interface 108. However, the shelf portions 334, 338 may have a greater length to generate a wider shelf area. In some examples, the shelf 130 or shelf 330 includes a material 342, such as a soft silicone, to provide a grip surface for an edge of the user interface 108.

The shelf 330 may further include stoppers, which are illustrated in the form of vertically extending edge pieces 346. The edge pieces 346 are sized and positioned within the shelf 330 to prevent the user interface 108 from sliding out of the user interface housing 10 horizontally. The position of the edge pieces 346 may be adjusted to accommodate various widths of user interfaces 108. Accordingly, the edge pieces 346 are adjustable along a horizontal plane to define different widths for retaining different user interfaces 108. In some examples, the edge pieces 346 may be dropped in and pivoted into a locked position on the shelf 330. Furthermore, the shelf 330 may include a plurality of indentations sized to receive the edge pieces 346 to lock the edge pieces 346 into position on the shelf 330. Alternatively, the edge pieces 346 may be slidably coupled with the shelf and locked into position with a fastener. Even further, the edge pieces 346 may be fixed and secured into position on the ends of the shelf 330. For example, the edge pieces 346 may be molded as an integral piece with the shelf 330.

One or both of the first shelf portion 334 and the second shelf portion 338, including the edge pieces 346, may be adjustable along a horizontal plane to define different widths to accommodate electronic devices of varying dimensions. For example, the body 18 of the user interface housing 10 may include a groove, a track, a slide, or a similar feature that engages the first shelf portion 334 and the second shelf portion 338. The first and second shelf portions 334, 338 define a first width when in a first position and a different second width when in a second position to accommodate user interfaces 108 having differing widths. The first and second shelf portions 334, 338 and/or the edge pieces 346 may be adjusted to minimize horizontal movement of the user interface 108 on the shelf 330, and thereby prevent removal of the user interface 108 from the user interface housing 10.

Use of the present device may provide for a variety of advantages. For example, the first and second projections 178, 182 each engage a sloped surface of the teeth 194. The sloped surface provides for downward movement of the locking body 46 while preventing upward movement. Additionally, the button 128 includes the first and second ribs 216, 220 that extend into the aperture 222 defined by the locking body 46. The first and second ribs 216, 220 prevent sliding movement of the button 128, and consequently, at least partially prevent pivoting of the latch mechanism 50. Limiting the pivoting of the latch mechanism 50 prevents the locking body 46 from moving toward the upper portion 22 of the body 18 of the user interface housing 10 while allowing movement toward the lower portion 26. This one directional movement secures the user interface 108 in the user interface housing 10 while preventing unwanted removal of the user interface 108 from the user interface housing 10. Further, the button 128 has a continuous arcuate surface that defines a shape complementary to the shape of the upper end 124 of the latch mechanism 50. The continuous arcuate surface reduces the ability of a user to grasp and move the button 128, providing further security for retaining the user interface 108. Moreover, the upper end 124 of the locking body 46 may define the access notch 250 for receiving the tool 254. In such examples, the locking body 46 may be adjusted toward the upper portion 22 of the body 18 in response to force being applied to the flexible body 150 by the tool 254. Moreover, the user interface housing 10 provides security for the user interface 108. These and other advantages may be realized and/or achieved.

According to one aspect of the present disclosure, a patient support apparatus includes a frame that has a head end and a foot end. A support arm is operably coupled to the head end of the frame. A cord is coupled to the support arm. A user interface housing is operably coupled to the cord and configured to retain a user interface. The user interface housing includes a locking body coupled to a body of the user interface housing and has a flange configured to engage an edge of the user interface. A latch mechanism includes a flexible body coupled to a rear side of the locking body. The latch mechanism is configured to selectively secure the locking body in a position. A shelf is coupled to a lower portion of the body of the user interface housing. The shelf has stoppers operably coupled to the shelf. The first and second stoppers are adjustable along a horizontal plane to define different widths.

According to another aspect, a flexible body includes first and second projections spaced apart from one another and coupled to one another via a connecting portion.

According to another aspect, an upper portion of a locking body defines an access notch for receiving a tool configured to apply a force to a connecting portion of a flexible body.

According to another aspect, a latch mechanism is adjustable between an extended position and a retracted position. A force applied by a tool adjusts the latch mechanism to the retracted position.

According to another aspect, a button defines a first rib and a second rib that extend from a rear side thereof. The first and second ribs extend through an aperture defined by a locking body.

According to another aspect, a button is operably coupled to first and second shafts. Each of the first and second shafts is disposed between first and second ribs.

According to another aspect, a flexible body includes first and second flexible tabs operably coupled with first and second shafts, respectively. Each of the first and second flexible tabs extends at least partially between the first and second shafts.

According to another aspect of the present disclosure, a user interface housing for a patient support apparatus includes a body that has an upper portion and a lower portion. First and second ribs extend between the upper portion and the lower portion. The first and second ribs define first and second channels, respectively. A locking body is slidably disposed between the first and second ribs. The locking body includes a latch mechanism configured to secure the locking body in position. The locking body defines an access notch configured to receive a tool for selectively releasing the latch mechanism.

According to another aspect, an access notch is positioned on an upper end of a rear side of a locking body.

According to another aspect, a locking body includes a flange defining a recess configured to retain an upper edge of a user interface.

According to another aspect, a latch mechanism includes a flexible body that has a first projection disposed adjacent a first aperture defined by a locking body. A second projection laterally spaced from the first projection and disposed adjacent a second aperture defined by the locking body and a connecting portion. The connecting portion couples the first and second projections.

According to another aspect, first and second projections move to a retracted position relative to the first and second apertures, respectively, upon downward movement of the connecting portion.

According to another aspect, a locking body is configured to slide between an upper portion and a lower portion when first and second projections are in a retracted position.

According to another aspect, a plurality of teeth are disposed within first and second channels, respectively. Each of the first and second projections is configured to engage at least one tooth surface when in an extended position.

According to another aspect, a shelf is disposed at a lower portion of the body.

First and second stoppers are operably coupled with the shelf. The first and second stoppers are configured to retain a lower edge of a user interface within the shelf.

According to another aspect, stoppers are adjustable on a shelf along a horizontal plane to define different widths.

According to another aspect of the present disclosure, a user interface housing for a patient support apparatus includes a body that has an upper portion and a lower portion. First and second ribs extend between the upper portion and the lower portion. The first and second ribs define first and second channels, respectively. A locking body is slidably engaged with the first and second ribs and is adjustable between the upper and lower portions. The locking body defines an aperture. A button is operably coupled with the locking body. The button includes at least one rib configured to extend through the aperture on the locking body to selectively limit movement of the locking body.

According to another aspect, at least one rib includes a first rib and a second rib spaced apart from one another. First and second ribs are sized to extend a height of an aperture.

According to another aspect, an upper end of a locking body is curved and extends outwardly from a planar portion.

According to another aspect, a button defines a shape complementary to a shape of an upper end. The button has a continuously arcuate outer surface.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A user interface housing for a patient support apparatus comprising:
    a body including an upper portion and a lower portion;
    first and second ribs extending between the upper portion and the lower portion, the first and second ribs defining first and second channels, respectively; and
    a locking body slidably disposed between the first and second ribs, the locking body including a latch mechanism configured to secure the locking body in position, wherein the locking body defines an access notch configured to receive a tool for selectively releasing the latch mechanism, and wherein the access notch is positioned on an upper end of a rear side of the locking body.

2. The user interface housing of claim 1, wherein the locking body includes a flange defining a recess configured to retain an upper edge of a user interface.

3. The user interface housing of claim 1, wherein the latch mechanism includes a flexible body comprising:
   a first projection disposed adjacent a first aperture defined by the locking body;
   a second projection laterally spaced from the first projection and disposed adjacent a second aperture defined by the locking body; and
   a connecting portion, wherein the connecting portion couples the first and second projections.

4. The user interface housing of claim 3, wherein the first and second projections move to a retracted position relative to the first and second apertures, respectively, upon downward movement of the connecting portion.

5. The user interface housing of claim 4, wherein the locking body is configured to slide between the upper portion and the lower portion when the first and second projections are in the retracted position.

6. The user interface housing of claim 3, further comprising:
   a plurality of teeth disposed within the first and second channels, respectively, each of the first and second projections is configured to engage at least one tooth surface when in an extended position.

7. The user interface housing of claim 1, further comprising:
   a shelf disposed at the lower portion of the body; and
   first and second stoppers operably coupled with the shelf, wherein the first and second stoppers are configured to retain a lower edge of a user interface within the shelf.

8. The user interface housing of claim 7, wherein the first and second stoppers are adjustable on the shelf along a horizontal plane to define different widths.

9. The user interface housing of claim 1, wherein the latch mechanism includes a flexible body coupled to the rear side of the locking body.

10. The user interface housing of claim 9, wherein the flexible body includes:
    first and second body portions laterally spaced from one another and extending along the rear side of the locking body; and
    first and second projections laterally spaced from one another on opposing sides of the locking body and extending outward from the first and second body portions and toward first and second apertures, respectively, defined by the locking body.

11. The user interface housing of claim 10, wherein the flexible body includes:
    a connecting portion including first and second arcs coupled to the first and second body portions, respectively, the connecting portion configured to be engaged by the tool to, consequently, withdraw the first and second projections from the first and second apertures to a retracted position.

12. The user interface housing of claim 9, further comprising:
    a plurality of teeth disposed within the first and second channels, respectively, each of the first and second projections have angled edges that engage sloped surfaces of the plurality of teeth to form a pawl, and wherein, in an extended position, the first and second projections extend outwardly from the first and second apertures to engage the plurality of teeth and catch on sloped edges to prevent motion toward the upper portion of the body.

13. The user interface housing of claim 1, further comprising:
    a shelf disposed at the lower portion of the body.

14. The user interface housing of claim 13, wherein the shelf includes a first shelf portion and a second shelf portion, each of the first and second shelf portions extending upwards to retain an edge of a user interface.

15. The user interface housing of claim 1, wherein the body includes a handle that extends from the upper portion to the lower portion.

* * * * *